United States Patent [19]

Chubb et al.

[11] 3,965,173

[45] June 22, 1976

[54] PROCESS FOR PREPARING p-(5-CHLORO-2-METHOXY-BENZAMIDOE-THYL)-BENZENE SULFONAMIDE

[76] Inventors: Francis L. Chubb, 4835 Pierre Lauzon, Pierre Fondes 910; Lucien Eric, 1141 Lucerne Road, Town of Mount Royal, Montreal 305, both of Canada

[22] Filed: May 21, 1971

[21] Appl. No.: 145,923

[52] U.S. Cl.................. 260/556 AR; 260/473 R; 260/473 S; 260/521 H; 260/543 R; 260/544 D; 260/553 DA; 260/559 S; 260/507 R
[51] Int. Cl.².................................... C07C 143/80
[58] Field of Search ........................ 260/556 AR

[56] References Cited
UNITED STATES PATENTS 3,055,904   9/1962   Graf et al.................... 260/556 AR
3,454,635   7/1969   Weber et al................. 260/556 AR

OTHER PUBLICATIONS

C.A. 51: 10425a (1957) Pasquino.
JACS 79: 2811–13 (1957) Shapiro et al.
C.A. 63: 8253g (1965) Davidova et al.
Synthetic Organic Chemistry (1953) Wagner et al. pp. 822–823.

Primary Examiner—Sherman D. Winters
Attorney, Agent, or Firm—Kevin B. Clarke

[57] ABSTRACT

A process for preparing p-[5-chloro-2-methoxy-benzamidoethyl]-benzene sulfonamide consisting of treating 5-chlorosalicylic acid or its ester by methylating and aminolysis to form N-phenethyl-5-chloro-2-methoxybenzamide followed by chlorosulfonation and aminolysis.

5 Claims, No Drawings

PROCESS FOR PREPARING P-(5-CHLORO-2-METHOXY-BENZAMIDOE-THYL)-BENZENE SULFONAMIDE

This invention relates to a process for preparing p-[5-chloro-2-methoxybenzamidoethyl]-benzene sulfonamide.

The sodium salt of the p-[5-chloro-2-methoxybenzamidoethyl]-benzene sulfonamide is the starting material for a number of processes for the preparation of 1-[p-(5-chloro-2-methoxybenzamidoethyl)-benzenesulfonyl]-3-cyclohexylurea more commonly known as glyburide; a particularly useful process is disclosed in co-pending application Ser. No. 144,271 filed May 17, 1971 wherein the sodium salt of p-[5-chloro-2-methoxybenzamidoethyl]-benzene sulfonamide is reacted with hydroxyethylcyclohexyl carbamate.

In view of the importance of p-[5-chloro-2-methoxybenzamidoethyl]-benzene sulfonamide it is desirable to have a process for its production involving the use of cheap, commercially available materials which process provides high yields and the present invention contemplates the use of 5 chlorosalicylic acid and phenethylamine, both of which are commercially available. In general terms the present invention provides a process for producing p-[5-chloro-2-methoxybenzamidoethyl]-benzene sulfonamide by methylation of 5 chlorosalicylic acid to form methyl 5-chloro-2-methoxybenzoate after which the latter is converted by aminolysis with phenethylamine to provide a new compound N-phenethyl-5-chloro-2-methoxybenzamide which is then converted by chlorosulfonation and aminolysis to the requisite p-[5-chloro-2-methoxybenzamidoethyl]-benzenesulfonamide.

It has been found that the new methylated amide referred to above, viz., N-phenethyl-5-chloro-2-methoxybenzamide may be obtained by forming the ester of 5-chlorosalicylic acid viz. methyl 5-chlorosalicylate and then methylating to form methyl 5-chloro-2-methoxybenzoate which is then subjected to aminolysis with phenethylamine to give the new methylated amide; the difference between the two procedures resides in the conditions under which methylating is conducted; it has been found that if methylation is conducted under anhydrous conditions, the 5-chlorosalicylic acid is methylated directly to give methyl 5-chloro-2-methoxybenzoate whereas if the methylation is conducted under aqueous conditions, it is necessary to first esterify the 5-chlorosalicylic acid.

A longer route, but one which also gives good yields of the new methylated benzamide though still involving aminolysis with phenethylamine, consists of the step of converting the methylated 5-chlorosalicylic acid or its ester via the acid and acid chloride followed by aminolysis to give the new methylated benzamide.

The reactions described above are illustrated in the following scheme:

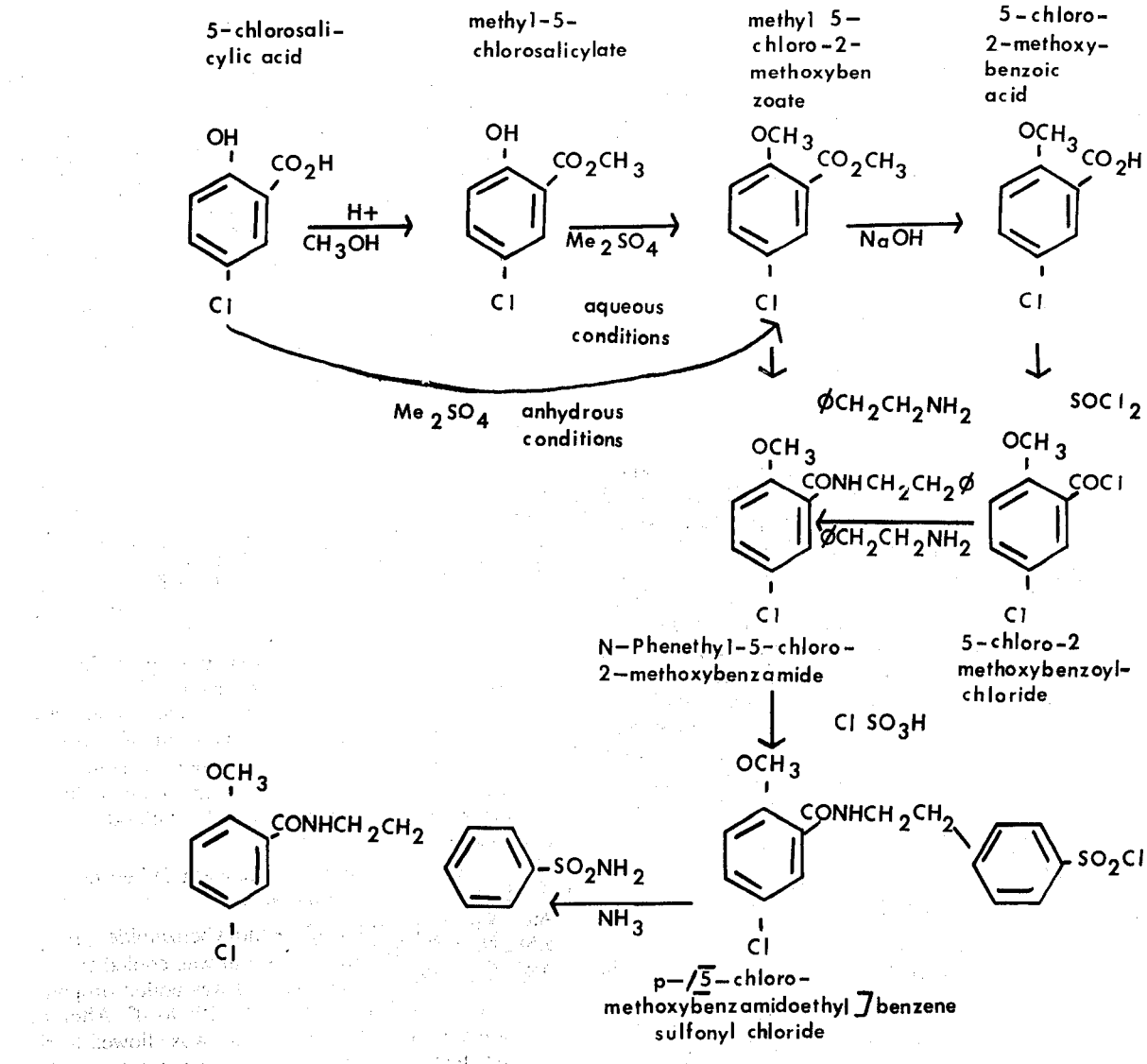

The invention will now be further illustrated by way of the following examples:

EXAMPLE 1

(via methylation of the ester and aminolysis)

a. Methyl 5-chlorosalicylate

5-Chlorosalicylic acid (5 kg.) dissolved in methanol (50 l.) and concentrated sulfuric acid (2 l.), was heated under reflux for 24 hours. The product crystallized when the solution was cooled in a dry ice/acetone mixture, and the solid when collected gave the ester (5 kg., 92%) sufficiently pure to use in the next step. Recrystallization give pure ester m.p. 45°–47°.

b. Methyl 5-chloro-2-methoxybenzoate

Aqueous sodium hydroxide (1650 ml., 2N) and dimethyl sulfate (335 g.) were added to a solution of methyl 5-chlorosalicylate (500 g.) in acetone (2750 ml.). The solution was stirred for 10 minutes and sodium hydroxide (825 ml., 2N) and dimethylsulfate (168 g.) were then added. The mixture was heated under reflux for 45 minutes and the acetone then evaporated under reduced pressure. The residue was extracted with ether and the ether extract was then washed with 5% aqueous sodium hydroxide. The extract was dried and the ether removed under reduced pressure. The residue was distilled to give the required methoxy ester (350 g., 66%), b.p. 105°–110°, 0.1mm.

c. N-Phenethyl-5-chloro-2-methoxybenzamide

A mixture of methyl-5-chloro-2-methoxybenzoate (200 g., 1 mole) and phenethylamine (240 g., 2 moles) was heated at 125° for 5 hours. Distillation of the reaction product gave the required amide (IV) in high yield (243 g., 84%) b.p. 200–220, 0.1 mm. A sample recrystallized from ether gave a solid m.p. 58°–61°. An analytical sample (LE-IV-172) was obtained by recrystallization from hexane/ethyl acetate and was a solid m.p. 62°–64°.

|  | C | H | N |
|---|---|---|---|
| $C_{16}H_{16}ClNO_2$ required: | 66.16 | 5.72 | 5.01 |
| found | 66.32 | 5.57 | 4.83 | d. p-(5-Chloro-2-methoxybanzamidoethyl)-benzene sulfonamide

N-phenethyl-5-chloro-2-methoxybenzamide (400 g.) was added slowly in small portions, with stirring at −10°, to chlorosulfonic acid (675 ml.). Upon completion of the addition the mixture was stirred and warmed on a steam bath for 45 minutes. The mixture was allowed to cool to room temperature before it was slowly poured onto crushed ice. The resulting gummy solid was separated from the water layer and added to concentrated ammonia (2 l.). This was then heated on the steam bath with stirring, and was then allowed to stand overnight at room temperature. The precipitate was filtered, washed with water, and then suspended in a mixture of water (1 l.) and aqueous hydrochloric acid (1 l., 6N). The solid was collected and washed with water, and the product recrystallized from glacial acetic acid (2 l.) to give the sulfonamide (357 g., 70%), m.p. 202°–206°.

EXAMPLE 2

(via acid and acid chloride)

a. 5-Chloro-methoxybenzoic acid

To a solution of methyl 5-chlorosalicylate (20 g.) in acetone 110 ml.) was added 2 N sodium hydroxide (66 ml.) and dimethyl sulphate (13.86 g.). The mixture was stirred for 10 minutes, sodium hydroxide 33 ml., 2N) and dimethyl sulphate (6.93 g.) added, and the mixture was heated under reflux for 45 minutes. The product was then cooled, the acetone evaporated off, and the residue was taken up in ether. The ether was extracted with dilute sodium hydroxide, evaporated off, and the residue heated under reflux for 1 hour with 10 aqueous sodium hydroxide (100 ml.). The product was cooled and acidified. The precipitate acid was filtered off and recrystallized from ethanol-water to give 8 g., m.p. 80°–81° (45%) with a second crop of 0.8 g., m.p. 77°–79° (4.5%).

b. 5-Chloro-2-methoxybenzoylchloride

5-Chloro-2-methoxybenzoic acid (19 g.) was heated in thionyl chloride 64 ml.) under reflux for 1 hour. Benzene (100 ml.) was then added, and evaporated off under reduced pressure. The solid residue was recrystallized from hexane to give the required product (15 g., 72%) m.p. 59°–60°.

c. N-Phenethyl-5-chloro-2-methoxybenzamide

5-Chloro-2-methoxybenzoyl chloride (15g.), dissolved in benzene, was added slowly to a solution of phenethylamine (18 g.) in benzene. Phenethylamine hydrochloride formed was filtered off, and the benzene removed from the filtrate. The residual oil was distilled to give an oil (19.4 g., 90%) b.p. 205° at 0.2 mm., which crystallized on standing m.p. 60°–63°.

EXAMPLE 3

(via methylation of the 5-chlorosalicylic acid)

Methyl 2-methoxy-5-chlorobenzoate

5Chlorosalicylic acid (100 g.), acetone (1 l.), and anhydrous potassium carbonate (315 g.) were stirred under reflux for 20 minutes. Dimethyl sulphate (215 g.) was then slowly added and the reaction mixture was stirred and heated under reflux for 4 hours. The product was cooled and the solid filtered off, and then the acetone was removed. Distillation under reduced pressure yielded a low boiling fraction consisting of unreacted dimethyl sulphate (b.p. 60°–80°) and methyl 5-chloro-2-methoxybenzoate (109 g., 95%) b.p. 135°–138° at 12 mm. pressure.

It has also been discovered that p-(5-chloro-2-methoxybenzamidoethyl)-benzenesulfonyl chloride may be produced by a method involving converting N-phenethyl-5-chloro-2-methoxybenzamide into p-(5-chloro-2-methoxybenzamidoethyl)-benzenesulfonic acid with subsequent treatment with thionyl chloride. The following examples illustrate the method:

p-(5-chloro-2-methoxybenzamidoethyl)-benzenesulfonic acid.

N-phenethyl-5-chloro-2-methoxybenzamide (10 g.) dissolved in 25 ml. of chloroform was cooled to −10° and 19 g. of chlorosulfonic acid was added dropwise, maintaining the temperature at −10° to 0°. After the addition was complete the mixture was allowed to rise to room temperature and it was poured onto cracked ice. The crude sulfonic acid was filtered and 7.3 g. (57%) was obtained. A sample recrystallized for analysis from alcohol-acetonitrile melted at 188°–189°. Anal. Calcd. for $C_{16}H_{16}ClNO_5S$: C, 51.94; H, 4.36; Cl, 9.58; N, 3.79; S, 8.67. Found: C, 50.10; H, 4.27; Cl, 9.93; N, 4.04; S, 8.84.

p-(5-chloro-2-methoxybenzamidoethyl)-benzenesulfonyl chloride.

A. From N-phenethyl-5-chloro-2-methoxybenzamide. N-phenethyl-5-chloro-2-methoxybenzamide (90 g.) was slowly added to 160 ml. of chlorosulfonic acid at −10°. The stirred mixture was heated 45 minutes on the steam bath. After cooling, the mixture was poured onto crushed ice. The gummy precipitate was filtered and dissolved in ether, from which it crystallized on standing. A total of 30.5 g. (24%), m.p. 99°–102° was obtained. A sample recrystallized from benzene melted at 107°–110°. Anal. Calcd. for $C_{16}H_{15}Cl_2NO_4S$: C, 49.50; H, 3.89; Cl, 18.27; N, 3.61; S, 8.25. Found: C, 49.61; H, 4.24; Cl, 17.95; N, 3.85; S, 8.22.

B. From p-(5-chloro-2-methoxybenzamidoethyl)-benzenesulfonic acid. A mixture of 10 g. of anhydrous p-(5-chloro-2-methoxybenzamidoethyl)-benzenesulfonic acid, 0.02 ml. of dimethylformamide and 5 ml. of thionyl chloride was warmed on the steam bath until the mixture was homogeneous. The excess thionyl chloride was evaporated under reduced pressure and the residual oil was dissolved in 20 ml. benzene. On cooling and concentrating 6.6 g. (63%) of the sulfonyl chloride, m.p. 107°–110° was obtained.

What is claimed is:

1. A process for preparing p-(2-{5-chloro-2-methoxybenzamido}ethyl)-benzene sulfonamide which comprises the steps of methylating 5-chlorosalicylic acid to methyl-5-chloro-2-methoxybenzoate, treating methyl-5-chloro-2-methoxybenzoate with phenethylamine to obtain N-phenethyl-5-chloro-2-methoxybenzamide, subjecting said N-phenethyl-5-chloro-2-methoxybenzamide to chlorosulfonation and aminolysis to yield p-(2-{5-chloro-2-methoxybenzamido ethyl)-benzene} sulfonamide.

2. A process as claimed in claim 1 wherein said 5-chlorosalicylic acid is esterified prior to methylation.

3. A process as claimed in claim 1 wherein said methylation is carried out under aqueous conditions.

4. A process as claimed in claim 1 wherein said methylation is carried out under non-aqueous conditions.

5. A process as claimed in claim 1 wherein said methyl-5-chloro-2-methoxybenzoate is subjected to alkaline hydrolysis followed by treatment with thionylchloride prior to reaction with phenethylamine.

* * * * *